United States Patent [19]
Negrisoli et al.

[11] Patent Number: 5,973,199
[45] Date of Patent: *Oct. 26, 1999

[54] HYDROSOLUBLE ORGANIC SALTS OF CREATINE

[75] Inventors: Gianpaolo Negrisoli; Lucno Del Corona, both of Bergamo, Italy

[73] Assignee: Flamma S.p.A., Bergamo, Italy

[*] Notice: This patent issued on a continued prosecution application filed under 37 CFR 1.53(d), and is subject to the twenty year patent term provisions of 35 U.S.C. 154(a)(2).

[21] Appl. No.: 08/649,620

[22] PCT Filed: Jul. 21, 1995

[86] PCT No.: PCT/EP95/02897

§ 371 Date: May 22, 1996

§ 102(e) Date: May 22, 1996

[87] PCT Pub. No.: WO96/04240

PCT Pub. Date: Feb. 15, 1996

[30] Foreign Application Priority Data

Aug. 4, 1994 [IT] Italy ............................ MI94A001693

[51] Int. Cl.⁶ .................................................. C07C 241/00
[52] U.S. Cl. ............................................................ 562/560
[58] Field of Search ............................................. 562/560

[56] References Cited

U.S. PATENT DOCUMENTS

| | | | |
|---|---|---|---|
| 1,967,400 | 7/1934 | Fischl | 562/560 |
| 4,420,432 | 12/1983 | Chibata | 562/560 |
| 5,091,171 | 2/1992 | Yu | 424/642 |
| 5,387,696 | 2/1995 | Kottenhahn | 548/533 |
| 5,489,589 | 2/1996 | Wittman | 514/232.8 |
| 5,627,172 | 5/1997 | Almada | 514/120 |

FOREIGN PATENT DOCUMENTS

| | | |
|---|---|---|
| 0 669 083 | 8/1995 | European Pat. Off. . |
| 53-6204 | 3/1978 | Japan ............. 562/560 |
| 94/02127 | 2/1994 | WIPO . |

OTHER PUBLICATIONS

Chemical Abstracts, vol. 84, No. 1, 1976 Columbus, Ohio, US; p. 13433.

ACTA Physiol. Scand. (1995), 153 (2), 207–9 Coden: APSCAX: ISSN: 0001–6772, 1995 Earnest, C.P. et al.

Primary Examiner—Michael L. Shippen
Attorney, Agent, or Firm—Griffin, Butler, Whisenhunt & Szipl,

[57] ABSTRACT

Hydrosoluble organic salts of creatine are disclosed. The salts are useful in the dietetic and food industry.

3 Claims, No Drawings

HYDROSOLUBLE ORGANIC SALTS OF CREATINE

The present invention refers to hydrosoluble organic salts of creatine of general formula I:

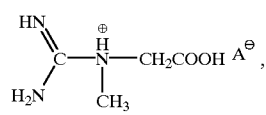

wherein $A^\ominus$ represents the anion of a mono, bi- or tricarboxylic acid. Preferred anions are the citrate, maleate, fumarate, tartrate or malate.

Creatine or N-(aminoiminomethyl)-N-methylglycine is a sarcosine derivative present in the muscle tissue of many vertebrates, man included, mainly combined with phosphoric acid in form of phosphorylcreatine and it is involved in the energy transfer from mitochondria to the ATP utilization sites.

Several studies indicate that there is a relationship between the creatine (phosphoryl creatine) concentration in the muscles having the function of keeping an high intracellular ATP/ADP ratio and maximum sustainable physical effort (Annu. Rev. Biochem. 54: 831–862, 1985; Science 24: 448–452, 1981; BESSMAN S. P., and F. SAVABI. The role of the phosphocreatine energy shuttle in exercise and muscle hypertrophy. In: Biochemistry of Exercise VII. A. W. Taylow, P. D. Gollnick, H. J. Green, C. D. Ianuzzo, E. G. Noble, G. Metivier, and J. R. Sutton., Intl. Series Sports Sciences 21: 167–178, 1990).

The creatine increase in diets may therefore be useful to bring the plasma creatine concentrations at levels providing significant values of creative itself in the muscle. The short creatine half-life in plasma (1–1.5 hours) makes however necessary to reach rapidly said levels and this, in view of the bioavailability degree of creatine, is obtainable only by the administration of high doses of 5–10 g (for mean body weights of 70 kg), amounts well tolerated because of the lack of toxicity of the compound.

The low solubility of creatine in water (1 g in 75 ml) is therefore a practical limitation to the possibility of marking immediately available in the specific diet the necessary amounts of creatine.

WO 94/02127, published on Feb. 3, 1994, discloses the use of creatine, optional combined with aminoacids or other components, in order to increase the muscle performance in mammals.

The present invention provides hydrosoluble stable organic salts of creatine of formula I characterized by high water solubility (from 3 to 15 times higher them that of creatine itself) and a process for their preparation. The salts of formula I are prepared by salifying creatine with the corresponding acids in aqueous or hydroalcoholic concentrated solution or in a water-immiscible solvent, at temperatures ranging from the room temperature to 50° C., optionally concentrating the solutions and filtering the crystallized salts. According to a preferred embodiment the salts of formula I are prepared by reacting creatine with an excess organic acid in ethyl acetate until the salt is completely formed, detectable with the IR analysis, cooling and filtering. The filtrated solvent, containing the excess acid is recycled and, after filling up of the components, is used for a further reaction.

The salts are characterized by IR, melting point, potentiometric and HPLC assay.

Table 1 reports the solubility of the salts I of the invention.

TABLE 1

| Creatine salt | Water solubility % (g/100 ml) |
|---|---|
| Citrate | 10 |
| Maleate | 19 |
| Fumarate | 3 |
| Tartarate | 8,5 |
| Malate | 4,5 |

EXAMPLE 1

39.45 g (0.18 mol) of monohydrate citric acid are suspended in 100 ml of ethyl acetate. 20 g (0.134 mol) of monohydrate creatine are added to the stirred suspension at 20–25° C. and the mixture is stirred 4 hours at 25° C. After IR control, the product is filtered and washed with ethyl acetate, then dried in oven at 50–55° C., obtaining 90% of salts, m.p. 112–114° C., 99.2% titer.

EXAMPLE 2

14.9 g (0.1 mol) of monohydrate creatine are added to a solution of 11.6 g (0,1 mol) of maleic acid in 20 ml of water. The so obtained solution is concentrated, cooled to 5° C. and the product filtered and dried under vacuum at 50° C., obtaining 87% of salt, m.p. 128–129° C., 99.8% titer.

We claim:

1. An isolated hydrosoluble salt of creatine of the formula:

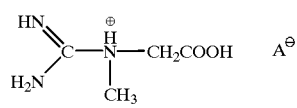

wherein $A^-$ represents the anion of citric, maleic, fumaric, or malic acid.

2. The hydrosoluble salt of claim 1, wherein $A^-$ is a citrate anion, said salt having a melting point of 112–114° C.

3. The hydrosoluble salt of claim 1, wherein $A^-$ is a maleate anion, said salt having a melting point of 128–129° C.

* * * * *

UNITED STATES PATENT AND TRADEMARK OFFICE
CERTIFICATE OF CORRECTION

PATENT NO. : 5,973,199
DATED : October 26, 1999
INVENTOR(S) : NEGRISOLI et al

It is certified that error appears in the above-identified patent and that said Letters Patent is hereby corrected as shown below:

On the title page item [75], change "Gianpaolo" to --Giampaolo-- and change "Lucno" to --Lucio--.

Signed and Sealed this

Twenty-eighth Day of March, 2000

Attest:

Q. TODD DICKINSON

*Attesting Officer*   *Commissioner of Patents and Trademarks*